United States Patent [19]
Strandberg

[11] Patent Number: 5,602,342
[45] Date of Patent: Feb. 11, 1997

[54] METHOD AND DEVICE FOR MEASURING THE FLOW OF AN ELECTROLYTIC FLUID

[75] Inventor: Hans Strandberg, Sundbyberg, Sweden

[73] Assignee: Pacesetter AB, Solna, Sweden

[21] Appl. No.: 677,910

[22] Filed: Jul. 10, 1996

Related U.S. Application Data

[63] Continuation of Ser. No. 511,524, Aug. 4, 1995, abandoned, which is a continuation of Ser. No. 177,933, Jan. 6, 1994.

[51] Int. Cl.⁶ .......................................................... A61B 5/00
[52] U.S. Cl. ........................................ 73/861.08; 128/691
[58] Field of Search ................................. 324/447, 449; 73/861.08, 861.09

[56] References Cited

U.S. PATENT DOCUMENTS

| | | |
|---|---|---|
| 3,450,984 | 6/1969 | Holmes . |
| 3,466,927 | 9/1969 | Magrini .................... 73/861.08 |
| 3,930,493 | 1/1976 | Williamson . |
| 4,484,582 | 11/1984 | Rottenberg et al. ............. 73/861.08 |
| 4,686,987 | 8/1987 | Salo et al. ..................... 128/419 PG |
| 5,174,299 | 12/1992 | Nelson . |

FOREIGN PATENT DOCUMENTS

| | | |
|---|---|---|
| 0077413 | 10/1981 | European Pat. Off. .......... G01F 1/56 |
| 0049027 | 4/1982 | European Pat. Off. . |
| 0310026 | 4/1989 | European Pat. Off. . |

Primary Examiner—Richard Chilcot
Assistant Examiner—Ronald L. Biegel
Attorney, Agent, or Firm—Hill, Steadman & Simpson

[57] ABSTRACT

In a method for measuring the flow of an electrolytic fluid, the voltage or current is measured between two stationary electrodes immersed in the electrolytic fluid. A device for measuring the flow has at least two electrodes intended for immersion in the electrolyte. The electrodes are stationary, and a measurement unit is arranged to measure the voltage or current between the electrodes.

29 Claims, 3 Drawing Sheets

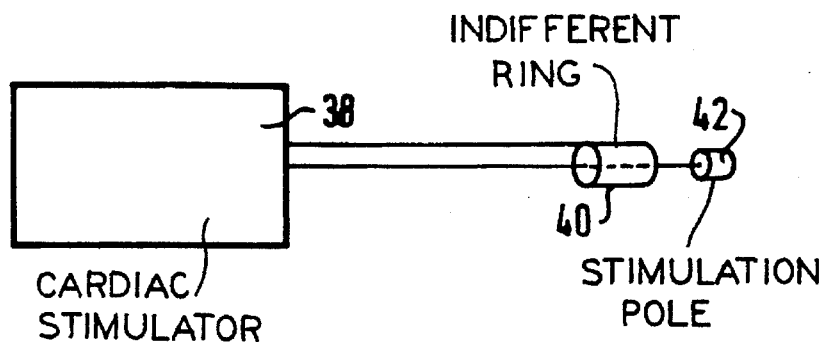
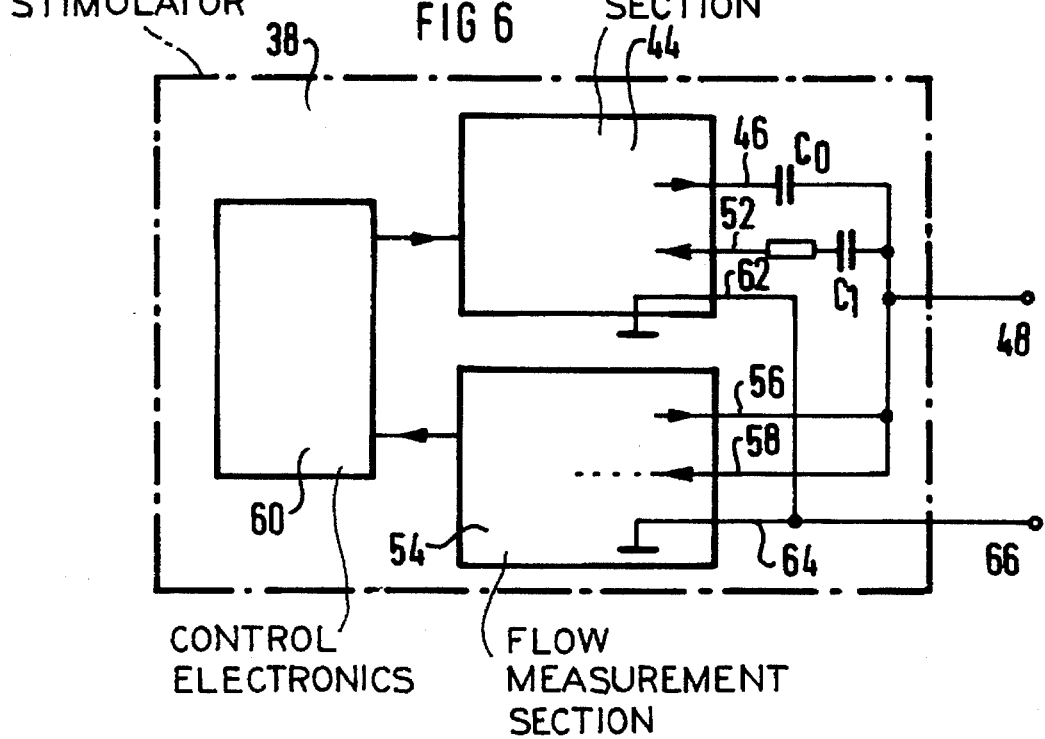
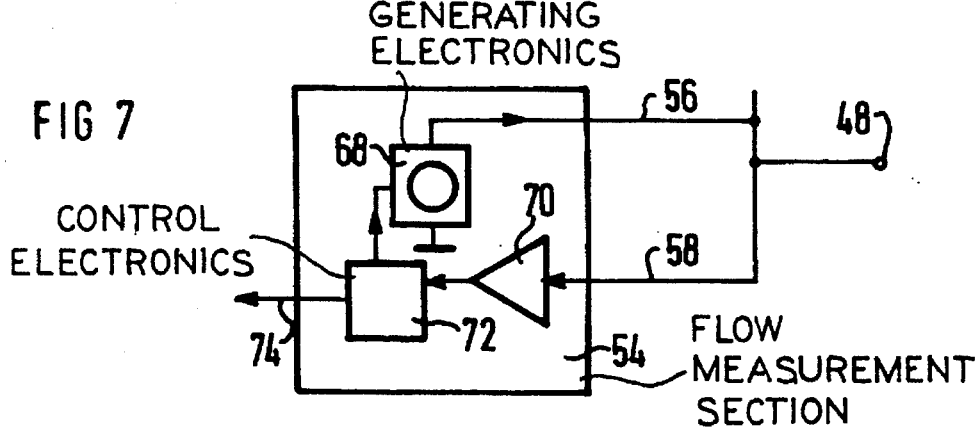

5,602,342

METHOD AND DEVICE FOR MEASURING THE FLOW OF AN ELECTROLYTIC FLUID

This is a continuation, of application Ser. No. 08/511,524, filed Aug. 4, 1995 now abandoned, which is a continuation, of application Ser. No. 08/177,933, filed Jan. 6, 1994.

BACKGROUND OF THE INVENTION

1. Field of the Invention

The present invention relates to a method and a device for measuring the flow of an electrolytic fluid, with at least two electrodes then being immersed in the electrolyte.

2. Description of the Prior Art

This type of flow measurement has a number of industrial and medical applications, such as the measurement of blood flow for rate-responsive control of a pacemaker and in conjunction with the detection of tachycardia. Blood flow is reduced in tachycardia.

This type of flow measurement has previously been performed by thermodilution, i.e., monitoring the cooling of a heated electrode by fluid flowing around it. The electrode can be heated and the temperature in the medium can be e.g. alternately sensed. Performing such flow measurements with the aid of Doppler sound measurement is also known. Both these prior art methods require relatively complex equipment.

SUMMARY OF THE INVENTION

An object of the present invention is to achieve a new method and a new device for measuring the flow of an electrolytic fluid which are considerably simpler and require simpler, and thus less expensive measurement equipment than known methods and devices.

The above object is achieved in accordance with the principles of the present invention in a method and apparatus for measuring the flow of an electrolytic fluid wherein the voltage or current between two stationary electrodes immersed in the electrolyte is measured.

The method and device according to the invention are based on the perception that an EMF develops between stationary electrodes when electrodes made of a suitable material are immersed in an electrolytic fluid, such as a saline solution. This EMF, or more accurately, the terminal voltages arising between the respective electrode and the electrolyte and giving rise to the resulting EMF, depends on the flow of fluid around the electrode.

The advantages of the invention lies in its simplicity. The measurement equipment required is simple, and an existing pacemaker electrode, if of the right type, can be employed when the invention is used for measurement of blood flow for pacemakers. A bipolar electrode with, e.g., a carbon tip and platinum ring, has been found to function very well for such measurement of blood flow according to the invention.

In a further embodiment of the method according to the invention, a continuous or repeatingly pulsed current, providing a net direct correct, is applied to the electrodes, and the resulting voltage between the electrodes, which depends on the flow of fluid, is measured. In this manner, the electrode system is "charged" with an EMF.

After a long period of time, the unloaded EMF amounts to about 40–50 mV. the measurement procedure, the system is pulsed with a few volts whose pulse duration lasts a fraction of 1 ms, an EMF of less than 1 mV arises with a recharge constant of the order of minutes.

In another embodiment of the method according to the invention, the pulse duration is regulated so the measured voltage becomes appropriate to the application in question.

Stimulation until a stable, elevated EMF is achieved, however, provides a very good possibility for detecting flow. The flow dependent variation in EMF amounts to about 50 mV.

Measurement of flow can also be performed by adjustment of the pulse amplitude in a compensating manner to keep the EMF voltage stable. Experiments have been made at a 0.5 V EMF and a 1 V EMF level. Changes in pulse voltage of 1–2 V were then required between a fast fluid flow and a stagnant fluid flow.

In another embodiment of the method according to the invention, the voltage between the electrodes is kept constant, and the current between the electrodes is measured. Since the charge transferred is a measure of the fluid flow, an increased fluid flow results in an increase in current.

No saturation has been observed. Both a zero flow current and sensitivity, i.e. current/flow rate, depend on the fluid and the electrodes used and the voltage applied. The measurement current is of the order of 50–500 nA.

When the invention is applied to a pacemaker, it must be kept in mind that the EMF, or terminal voltage, is greatly dependent on the stimulation pulses emitted. However, compensating for this is not very difficult, since the stimulation rate is deterministic and measurable, and measurement of current or voltage is performed immediately prior to the emission of a stimulation pulse according to a further embodiment of the method according to the invention. Studies have shown that the post-polarization course is not dependent on the fluid flow.

The voltage, which can be characterized as electrode EMF, is material-dependent. A reduction reaction, harmless to the electrode material, occurs at the negative electrode. However, an oxidation occurring at the positive electrode can cause dissolution of the material, i.e. the electrode can be eaten away. Thus, the positive electrode must be made of a non-reactive material. Therefore, the choice of electrode material must be made with care, as well as the choice of current direction, for the flow measurement.

According to an embodiment of the device of the invention when used with pacemakers, the electrodes each consist of a bipolar pacemaker electrode with a carbon tip and a platinum ring. Practical tests with this electrode configuration have yielded excellent flow measurement results.

DESCRIPTION OF THE DRAWINGS

FIG. 5 schematically depicts a pacemaker or defibrillator with the device according to the invention.

FIG. 6 is a block diagram of a pacemaker or defibrillator with the device according to the invention.

FIG. 7 is a block diagram of an example of the flow measurement device according to the invention in the version shown in FIG. 6.

DESCRIPTION OF THE PREFERRED EMBODIMENTS

Figure 1:
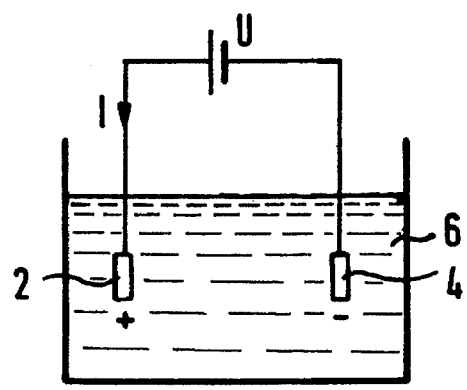
FIG. 1 shows a pair of electrodes in an electrolyte to illustrate the basic principle of the present invention.

FIG. 1 shows two stationary electrodes 2 and 4 immersed in an electrolytic fluid 6, e.g. a 0.5% saline solution.

When suitable electrodes are chosen, an EMF, which depends on the flow of the electrolytic fluid 6, develops between the electrodes 2 and 4. More precisely flow-dependent terminal voltages develop between each of the electrodes 2 and 4 and the electrolytic fluid, resulting in the EMF.

In FIG. 1, a voltage U is applied across the electrodes 2 and 4, and the current I is intended to be measured and its magnitude constitutes a measure of the flow of the electrolytic fluid.

The principle of the invention can be illustrated with the device shown in FIG. 1 by stirring the electrolytic fluid 6 with, e.g., a magnetic stirrer in order to provide a flow in the container of the electrolytic fluid 6.

Figure 2:
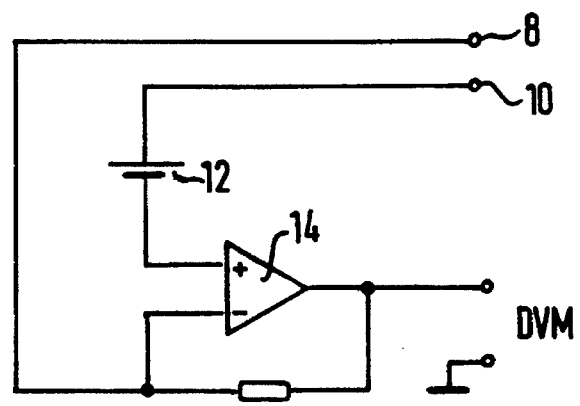
FIG. 2 shows an example of a circuit for performing the voltage measurement required for determining the flow in accordance with the principles of the present invention.

The current I through the pair of electrodes (regarded as corresponding voltage) can be measured with the circuit shown in FIG. 2, a suitable recording instrument being connected across output DVM. A reference image memory oscilloscope, i.e. an oscilloscope supplied with a normal pulse to which measured pulses can be compared to make deviations readily discernible to the eye, can be used as such a recording instrument.

When the circuit in FIG. 2 is used in a pacemaker with a bipolar electrode, the output terminal 8 is connected to the tip of the stimulating electrode, appropriately a carbon tip, and the output terminal 10 is connected to the sensing electrode, appropriately a platinum ring. The control voltage is supplied by the voltage source 12, and the voltage between output terminals 8 and 10 is measured with the feedback amplifier 14.

A lack of dissolved oxygen in the electrolytic fluid has been found to produce unstable, non-reproducible results. Oxygen must be present dissolved in the electrolytic fluid if flow measurement according to the invention is to operate reliably. Moreover, the pH value of the electrolyte has been found to affect the sensitivity of flow measurement. The limit value for reliable measurement with the method and device according to the invention is a pH of about 5, a more acidic solution impairing sensitivity. The processes at the two electrodes are:

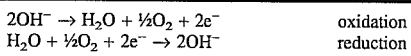

| | |
|---|---|
| $2OH^- \rightarrow H_2O + \frac{1}{2}O_2 + 2e^-$ | oxidation |
| $H_2O + \frac{1}{2}O_2 + 2e^- \rightarrow 2OH^-$ | reduction |

With a constant voltage between the two electrodes, any change in the normal potential of an electrode will also cause a change in the normal potential of the other electrode. The sensitivity to voltage changes of the oxidation process above increases as the solution becomes more acidic due to the lower concentration of hydroxide ions.

Experiments have also shown that the flow sensing primarily occurs at the positive electrode, whereas the negative electrode controls the current.

Figure 3:
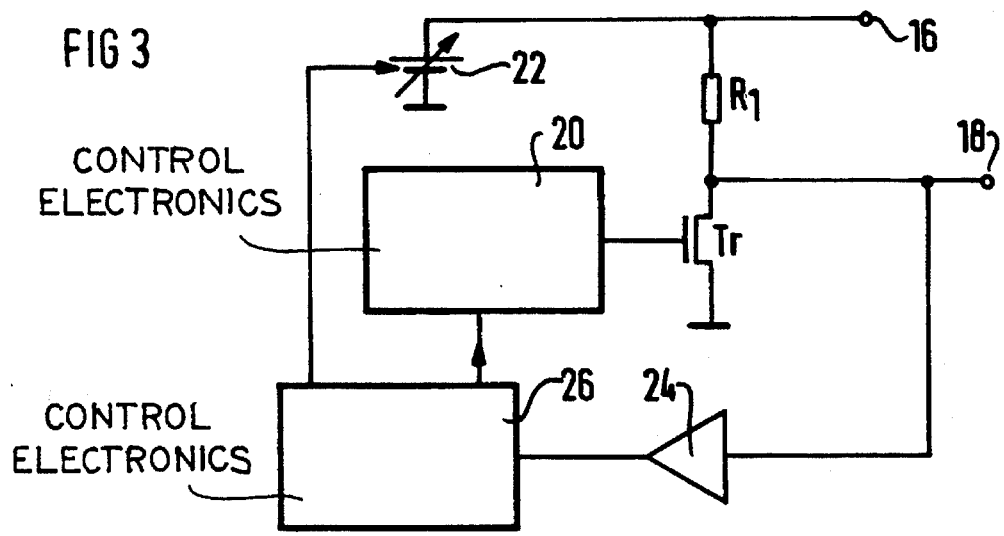
FIGS. 3 and 4 respectively show examples of measurement circuits in the device according to the invention.

FIG. 3 shows a version of the device according to the invention, intended for use in a pacemaker, for the measurement of blood flow. This embodiment is intended for pulsed or sampled flow measurement.

In the circuit according to FIG. 3, the output terminal 16 is connected to the indifferent electrode, suitably a platinum ring, and the output terminal 18 to the stimulation electrode, suitably a carbon tip, cf. the description of FIG. 2.

A high-resistance resistor $R_1$ is connected between the output terminals 16 and 18, and the electrode connected to the output terminal 18 is charged with charging pulses by the switching transistor Tr. Thus, these pulses are emitted by the same electrode as the pacemaker's stimulation pulses but at different times.

The switching transistor Tr is controlled by the control electronics 20.

An FET amplifier 24 and the following measurement and control electronics 26 are connected to the output terminal 18 to control the voltage source 22 and for the measurement. The measurement and control electronics 26 are further connected to the control electronics 20 of the transistor Tr. In this way control of both the transistor Tr and the voltage source 22 is possible depending on the voltage measured.

Figure 4:
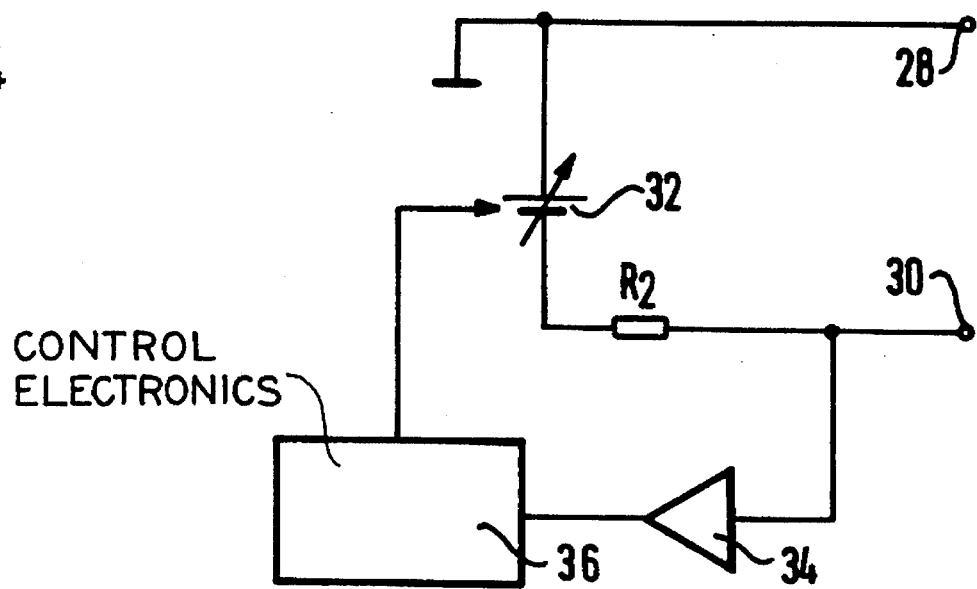

FIG. 4 shows an embodiment intended for continuous supply of current to the electrodes. In this embodiment, the indifferent electrode is connected to the output terminal 28 and the stimulation electrode to the output terminal 30.

The source of voltage 32, connected in series with a high resistance resistor $R_2$, is connected between the output terminals 28 and 30.

In the corresponding manner as in the version in FIG. 3, an FET amplifier 34 and following measurement and control electronics 36 are connected to the output terminal 30 for measurement and control purposes. Also in this instance, the source of voltage 32 is controllable, depending on the voltage measured between the electrodes.

FIG. 5 shows a cardiac pacemaker or defibrillator, with a conventional bipolar lead with an indifferent ring 40 and a stimulation pole 42. The cardiac stimulator 38 is equipped with a device according to the invention, and the ring 540 for this purpose is appropriately made of platinum and the pole 42 of carbon.

Practical tests have been made with a platinum ring with a contact area of about 32 mm² and a carbon tip with a 6 mm² contact area.

FIG. 6 shows a block diagram of the cardiac stimulator 38 of FIG. 5 in the form of a pacemaker. It will be understood by those skilled in the art that the pacemaker section can be replaced by a defibrillator section, or a defibrillator section could be provided in the cardiac stimulator 38 in addition to the pacemaker section.

The pacemaker section 44 is connected, via an output capacitor $C_0$, to the output terminal 48 for the stimulation electrode. Heart signals are received at the same output terminal 48 and are supplied via a filter 50 with a capacitor $C_1$ to the pacemaker section 44 via its input 52 for heart signal detection.

The cardiac stimulator 38 further contains a flow measurement unit 54 with an output 56 connected to the output 48 in order to supply the stimulation electrode with a bias signal in conjunction with the flow measurement. The voltage measurement signal required for measurement of the flow is received by the flow measurement unit via the input terminal 58.

Control electronics 60 are provided to control the pacemaker section 44, in response to the flow measurement unit 54.

Both the pacemaker section 44 and the flow measurement unit 54 are further connected, via outputs 62 and 64, to the output 66, intended to be connected to the indifferent electrode 40 in FIG. 5.

FIG. 7 shows the flow measurement unit 54 in greater detail. The flow measurement unit 54 contains signal generating electronics 68 for supplying, via the output 56 and the output 48, the electrode with currents or voltages required for measurement of the flow, as discussed above. The measurement signal for the flow measurement is received via the output 48 and the input 58 and is sent via a buffer amplifier 70 to the measurement and control electronics 72, which treat and analyze the measurement signal in an appropriate manner and deliver an output signal on the output 74 representing the measured flow value. The measurement and control electronics 72 are also connected to the signal-generating electronics 68 to control their function, in response to the measurement signals received.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for measuring a change in the flow of an electrolytic fluid consisting of the steps:

connecting two stationary electrodes respectively to opposite poles of a power source;

immersing said two stationary electrodes spaced from each other in an electrolytic fluid whose flow is to be measured and briefly producing respective electrochemical reactions at each stationary electrode in said electrolytic fluid, said reactions having an equilibrium condition at a reference flow of said electrolytic fluid;

measuring an electrical characteristic arising between said two stationary electrodes as a result of the flow of said electrolytic fluid causing a change in said electrical characteristic from said equilibrium condition by supplying a continuous current to said two stationary electrodes and measuring a resulting voltage between said electrodes; and identifying changes in said flow of said electrolytic fluid from said reference flow exclusively from the measurement of said electrical characteristic while maintaining said electrodes stationarily immersed in said electrolytic fluid.

2. A method for measuring a change in the flow of an electrolytic fluid consisting of the steps:

connecting two stationary electrodes respectively to opposite poles of a power source;

immersing said two stationary electrodes spaced from each other in an electrolytic fluid whose flow is to be measured and briefly producing respective electrochemical reactions at each stationary electrode in said electrolytic fluid, said reactions having an equilibrium condition at a reference flow of said electrolytic fluid;

measuring an electrical characteristic arising between said two stationary electrodes as a result of the flow of said electrolytic fluid causing a change in said electrical characteristic from said equilibrium condition by supplying a pulsed current between 10 and 500 nA to said two stationary electrodes and measuring a resulting voltage between said electrodes; and identifying changes in said flow of said electrolytic fluid from said reference flow exclusively from the measurement of said electrical characteristic while maintaining said electrodes stationarily immersed in said electrolytic fluid.

3. A method as claimed in claim 2 wherein the step of supplying a pulsed current to said two stationary electrodes is further defined by supplying said pulsed current as polarized pulses to said two stationary electrodes, each pulse having a pulse duration, and adjusting the pulse duration for obtaining a voltage of an appropriate magnitude for measurement.

4. A method for measuring a change in the flow of an electrolytic fluid consisting of the steps:

connecting two stationary electrodes respectively to opposite poles of a power source;

immersing said two stationary electrodes spaced from each other in an electrolytic fluid whose flow is to be measured and briefly producing respective electrochemical reactions at each stationary electrode in said electrolytic fluid, said reactions having an equilibrium condition at a reference flow of said electrolytic fluid;

measuring an electrical characteristic arising between said two stationary electrodes as a result of the flow of said electrolytic fluid causing a change in said electrical characteristic from said equilibrium condition by applying a constant voltage between said two stationary electrodes and measuring the current between said electrodes; and identifying changes in said flow of said electrolytic fluid from said reference flow exclusively from the measurement of said electrical characteristic while maintaining said electrodes stationarily immersed in said electrolytic fluid.

5. A method as claimed in claim 1 for use in an implantable cardiac stimulator for measuring blood flow, comprising the additional step of delivering a stimulation pulse to a patient in whom blood flow is to be measured, and wherein the step of measuring at least one of the voltage or current between said two stationary electrodes is further defined by generating a measurement of blood flow in said patient by measuring said current or voltage between said two stationary electrodes immersed in said blood flow immediately prior to generating said stimulation pulse.

6. An apparatus for measuring the flow of an electrolytic fluid consisting of:

two electrodes;

means for stationarily immersing said two electrodes in an electrolytic fluid whose flow is to be measured;

a pulsed power source means, having opposite poles to which said two stationary electrodes are respectively connected, for producing respective electrochemical reactions at each stationary electrode in said electrolytic fluid, said reactions having an equilibrium condition at a reference flow of said electrolytic fluid by applying a pulsed voltage across said two stationary electrodes of between 0.3 and 1.0 V; and means for measuring a current between said electrodes arising as a result of the flow of said electrolytic fluid causing a change in said electrical characteristic from said equilibrium condition and for identifying changes in said flow of said electrolytic fluid from said reference flow exclusively from the measurement of said electrical characteristic.

7. An apparatus for measuring the flow of an electrolytic fluid consisting of:

two electrodes;

means for stationarily immersing said two electrodes in an electrolytic fluid whose flow is to be measured;

a pulsed power source means, having opposite poles to which said two stationary electrodes are respectively connected, for producing respective electrochemical reactions at each stationary electrode in said electrolytic fluid, said reactions having an equilibrium condition at a reference flow of said electrolytic fluid by supplying current pulses of between 50 and 500 nA to one of said stationary electrodes; and means for measuring a voltage between said stationary electrodes, said pulses each having a pulse duration for generating a voltage appropriate for measurement between said electrodes arising as a result of the flow of said electrolytic fluid causing a change in said electrical characteristic from said equilibrium condition and for identifying changes in said flow of said electrolytic fluid from said reference flow exclusively from the measurement of said electrical characteristic.

8. An apparatus as claimed in claim 6 for use in a pacemaker for measuring blood flow, wherein said electrodes comprise respective poles of a bipolar pacemaker lead, said poles respectively consisting of carbon and platinum.

9. A method for measuring a change in the flow of an electrolytic fluid consisting of the steps:

connecting two stationary electrodes respectively to opposite poles of a power source;

immersing said two stationary electrodes spaced from each other in an electrolytic fluid whose flow is to be measured and briefly producing respective electrochemical reactions at each stationary electrode in said electrolytic fluid, said reactions having an equilibrium condition at a reference flow of said electrolytic fluid;

measuring an electrical characteristic arising between said two stationary electrodes as a result of the flow of said electrolytic fluid causing a change in said electrical characteristic from said equilibrium condition by applying a voltage pulse between 0.3 and 1.0 V across said two stationary electrodes and measuring a resulting current between said electrodes; and identifying changes in said flow of said electrolytic fluid from said reference flow exclusively from the measurement of said electrical characteristic while maintaining said electrodes stationarily immersed in said electrolytic fluid.

10. A method as claimed in claim 1 wherein the step of supplying a continuous current to said two stationary electrodes comprises supplying a current between 10 and 500 nA between said two stationary electrodes.

11. A method as claimed in claim 1 wherein the step of immersing said two stationary electrodes spaced from each other in an electrolytic fluid whose flow is to be measured comprises immersing said two stationary electrodes spaced from each other in an electrolytic fluid having a pH of about 5 or more.

12. A method for measuring a change in the flow of an electrolytic fluid consisting of the step;

connecting two stationary electrodes respectively to opposite poles of a power source;

immersing said two stationary electrodes spaced from each other in an electrolytic fluid whose flow is to be measured and briefly producing respective electrochemical reactions at each stationary electrode in said electrolytic fluid, said reactions having an equilibrium condition at a reference flow of said electrolytic fluid;

measuring an electrical characteristic, selected from the group consisting of voltage and current, arising between said two stationary electrodes as a result of the flow of said electrolytic fluid causing a change in said electrical characteristic from said equilibrium condition by applying a voltage of between 0.3 and 1.0 V across said two stationary electrodes and a current of between 50 and 500 nA between said two stationary electrodes; and identifying changes in said flow of said electrolytic fluid from said reference flow exclusively from the measurement of said electrical characteristic while maintaining said electrodes stationarily immersed in said electrolytic fluid.

13. A method as claimed in claim 12 wherein the step of immersing said two stationary electrodes spaced from each other in an electrolytic fluid whose flow is to be measured comprises immersing said two stationary electrodes spaced from each other in an electrolytic fluid having a pH of about 5 or more.

14. An apparatus used in a pacemaker for measuring blood flow consisting of:

a bipolar pacemaker lead having two poles;

means for stationarily immersing said two poles in a blood flow whose flow is to be measured;

a power source means, having opposite poles to which said two stationary poles are respectively connected, for producing respective electrochemical reactions at each stationary pole in said blood, said reactions having an equilibrium condition at a reference flow of said blood, by applying a continuous current to said two stationary poles; and means for measuring a voltage between said stationary arising as a result of the blood flow causing a change in said electrical characteristic from said equilibrium condition and for identifying changes in said blood flow from said reference flow exclusively from the measurement of said voltage.

15. An apparatus as claimed in claim 6 wherein said means for stationarily immersing said two electrodes in an electrolytic fluid whose flow is to be measured comprises means for stationarily immersing said two electrodes in an electrolytic fluid having a pH of about 5 or more.

16. An apparatus for measuring the flow of an electrolytic fluid consisting of:

two electrodes;

means for stationarily immersing said two electrodes in an electrolytic fluid whose flow is to be measured;

a power source means, having opposite poles to which said two stationary electrodes are respectively connected, for producing respective electrochemical reactions at each stationary electrode in said electrolytic fluid, said reactions having an equilibrium condition at a reference flow of said electrolytic fluid by producing a voltage across said two stationary electrodes of between 0.3 and 1.0 V and producing a current between said two stationary electrodes of between 50 and 500 nA; and means for measuring an electrical characteristic, selected from the group consisting of voltage and current, between said electrodes arising as a result of the flow of said electrolytic fluid causing a change in said electrical characteristic from said equilibrium condition and for identifying changes in said flow of said electrolytic fluid from said reference flow exclusively from the measurement of said electrical characteristic.

17. An apparatus as claimed in claim 16 wherein said means for stationarily immersing said two electrodes in an electrolytic fluid whose flow is to be measured comprises means for stationarily immersing said two electrodes in an electrolytic fluid having a pH of about 5 or more.

18. A method as claimed in claim 3 for use in an implantable cardiac stimulator for measuring blood flow, comprising the additional step of delivering a stimulation pulse to a patient in whom blood flow is to be measured, and wherein the step of measuring said electrical characteristic is further defined by generating a measurement of blood flow in said patient by measuring said electrical characteristic between said two stationary electrodes immersed in said blood flow immediately prior to generating said stimulation pulse.

19. A method as claimed in claim 3 wherein the step of immersing said two stationary electrodes spaced from each other in an electrolytic fluid whose flow is to be measured comprises immersing said two stationary electrodes spaced from each other in an electrolytic fluid having a pH of about 5 or more.

20. A method as claimed in claim 4 for use in an implantable cardiac stimulator for measuring blood flow, comprising the additional step of delivering a stimulation pulse to a patient in whom blood flow is to be measured, and wherein the step of measuring said electrical characteristic is further defined by generating a measurement of blood flow in said patient by measuring said electrical characteristic between said two stationary electrodes immersed in said blood flow immediately prior to generating said stimulation pulse.

21. A method as claimed in claim 4 wherein the step of immersing said two stationary electrodes spaced from each other in an electrolytic fluid whose flow is to be measured comprises immersing said two stationary electrodes spaced from each other in an electrolytic fluid having a pH of about 5 or more.

22. A method as claimed in claim 9 for use in an implantable cardiac stimulator for measuring blood flow, comprising the additional step of delivering a stimulation pulse to a patient in whom blood flow is to be measured, and wherein the step of measuring said electrical characteristic is further defined by generating a measurement of blood flow in said patient by measuring said electrical characteristic between said two stationary electrodes immersed in said blood flow immediately prior to generating said stimulation pulse.

23. A method as claimed in claim 9 wherein the step of immersing said two stationary electrodes spaced from each other in an electrolytic fluid whose flow is to be measured comprises immersing said two stationary electrodes spaced from each other in an electrolytic fluid having a pH of about 5 or more.

24. An apparatus as claimed in claim 13 wherein said power source means comprises means for producing a current between said two stationary electrodes of between 50 and 500 nA.

25. An apparatus as claimed in claim 14 wherein said stationary poles respectively consist of carbon and platinum.

26. An apparatus as claimed in claim 14 wherein said means for stationarily immersing said two poles in said blood flow to be measured comprises means for stationarily immersing said two poles in blood having a pH of about 5 or more.

27. An apparatus for use in a pacemaker for measuring blood flow consisting of:

a bipolar pacemaker lead having two poles;

means for stationarily immersing said two ploes in a blood flow whose flow is to be measured;

a pulsed power source means, having opposite poles to which said two stationary poles are respectively connected, for producing respective electrochemical reactions at each stationary pole in said blood, said reactions having an equilibrium condition at a reference flow of said blood, by applying a constant voltage between said two stationary poles; and means for measuring a current between said electrodes arising as a result of the blood flow causing a change in said electrical characteristic from said equilibrium condition and for identifying changes in said blood flow from said reference flow exclusively from the measurement of said current.

28. An apparatus as claimed in claim 27 wherein said stationary poles respectively consist of carbon and platinum.

29. An apparatus as claimed in claim 27 wherein said means for stationarily immersing said two poles in said blood whose flow is to be measured comprises means for stationarily immersing said two poles in blood having a pH of about 5 or more.

* * * * *